US006266549B1

(12) United States Patent
Melnikoff et al.

(10) Patent No.: US 6,266,549 B1
(45) Date of Patent: Jul. 24, 2001

(54) APPARATUS AND METHOD FOR EVALUATING CARDIAC FUNCTIONS

(75) Inventors: Donald J. Melnikoff, West Allis; Robert L. Young, Waukesha, both of WI (US)

(73) Assignee: Heska Corporation, Ft. Collins, CO (US)

( * ) Notice: Subject to any disclaimer, the term of this patent is extended or adjusted under 35 U.S.C. 154(b) by 0 days.

(21) Appl. No.: 09/230,666

(22) Filed: Jan. 29, 1999

Related U.S. Application Data

(63) Continuation-in-part of application No. 09/020,475, filed as application No. PCT/US98/08271 on Apr. 24, 1998, which is a continuation-in-part of application No. 08/546,246, filed on Oct. 20, 1995, now Pat. No. 5,715,816, which is a continuation-in-part of application No. 08/412,287, filed on Mar. 28, 1995, now Pat. No. 5,743,261, which is a continuation-in-part of application No. 08/163,052, filed on Dec. 6, 1993, now Pat. No. 5,417,207.

(60) Provisional application No. 60/045,006, filed on Apr. 25, 1997, and provisional application No. 60/067,810, filed on Dec. 5, 1997.

(51) Int. Cl.[7] ............................................. A61B 5/042
(52) U.S. Cl. ................................. 600/380; 607/124
(58) Field of Search ................................ 600/373–381; 607/115–122, 124, 137, 147

(56) References Cited

U.S. PATENT DOCUMENTS

| 1,103,669 | * | 7/1914 | Gibbs | 607/147 |
| 3,951,136 | | 4/1976 | Wall . | |
| 4,095,601 | * | 6/1978 | Aufranc | 607/72 |
| 4,176,660 | | 12/1979 | Mylrea et al. . | |
| 4,304,240 | | 12/1981 | Perlin . | |
| 4,349,031 | | 9/1982 | Perlin . | |
| 4,369,794 | | 1/1983 | Furler . | |
| 4,476,872 | | 10/1984 | Perlin . | |

(List continued on next page.)

FOREIGN PATENT DOCUMENTS

| 2003138 | * | 7/1971 | (DE) | 600/380 |
| 0 366 127 | | 10/1989 | (DE) . | |
| 1454066 | | 1/1975 | (GB) . | |
| WO 96/29927 | | 10/1996 | (WO) . | |

*Primary Examiner*—Lee Cohen
(74) *Attorney, Agent, or Firm*—Snell & Wilmer L.L.P.

(57) ABSTRACT

An electrode useful for generating electrical signals generally comprises a base and more than one dome-like protuberance on an exterior surface of the annular ring-like base. The electrodes can be utilized in connection with various probe applications. For example, the electrodes can be utilized with a probe adapted for insertion into an anatomical canal, e.g. the esophagus of an animal or a human for ECG or cardiac output measurements. An exemplary probe generally comprises a chassis with an electrical cable extending from the proximal end of the chassis and with the cable terminating at an electrical plug configured for connection to a cardiac monitor. The probe also includes an electrode assembly comprising the dome-like protuberances and configured to generate or receive electrical signals that are indicative of the cardiac functions of the patient. The probe may further include an engagement device attached to the chassis for stabilizing the probe within the esophagus. The probe may also be configured to include other sensing devices, for example, a temperature measuring device and an acoustic monitor.

17 Claims, 8 Drawing Sheets

U.S. PATENT DOCUMENTS

| | | |
|---|---|---|
| 4,559,951 | 12/1985 | Dahl et al. . |
| 4,706,688 | 11/1987 | Michael et al. . |
| 4,817,611 | 4/1989 | Arzbaecher et al. . |
| 4,819,647 * | 4/1989 | Byers et al. ............ 607/116 |
| 4,836,214 | 6/1989 | Sramek . |
| 5,109,851 | 5/1992 | Jadvar et al. . |
| 5,170,803 | 12/1992 | Hewson et al. . |
| 5,197,491 | 3/1993 | Anderson et al. . |
| 5,199,433 | 4/1993 | Metzger et al. . |
| 5,275,162 | 1/1994 | Edwards et al. . |
| 5,324,322 * | 6/1994 | Grill, Jr. et al. ............ 607/118 |
| 5,387,232 | 2/1995 | Trailer . |
| 5,394,880 | 3/1995 | Atlee, III . |
| 5,395,363 * | 3/1995 | Billings et al. ............ 606/41 |
| 5,431,696 | 7/1995 | Atlee, III . |
| 5,556,425 | 9/1996 | Hewson et al. . |
| 5,749,833 | 5/1998 | Hakki et al. . |
| 5,919,220 * | 7/1999 | Stieglitz et al. ............ 607/118 |
| 5,967,977 * | 10/1999 | Mullis et al. ............ 600/380 |

* cited by examiner

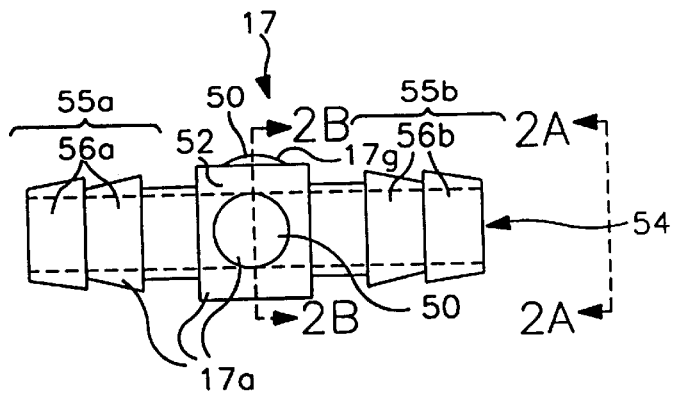
FIG. 2
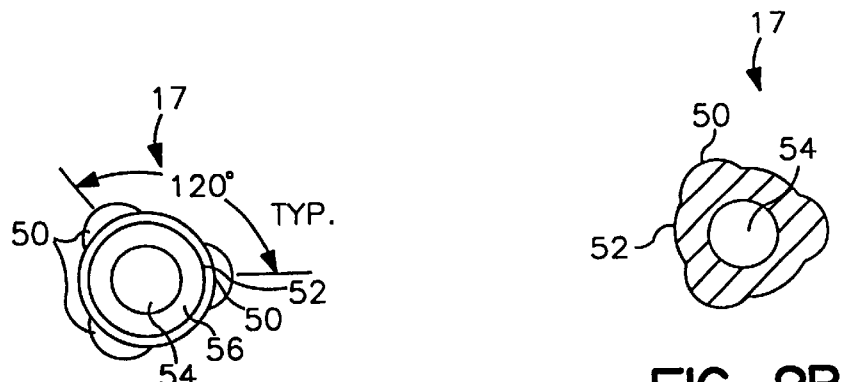
FIG. 2A
FIG. 2B
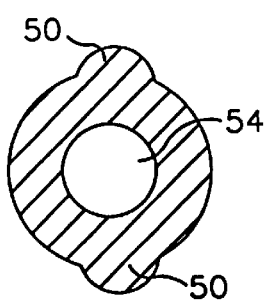
FIG. 3
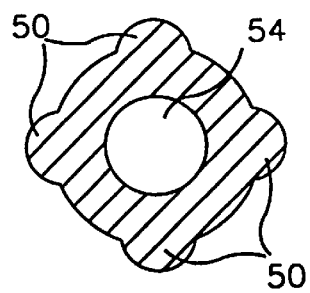
FIG. 4
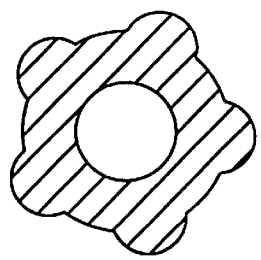
FIG. 5

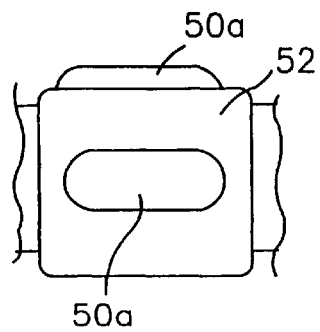 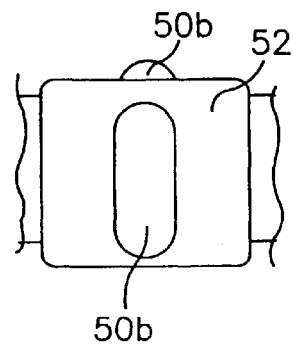
FIG. 6A  FIG. 6B
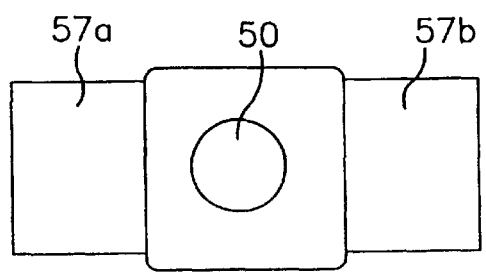
FIG. 7
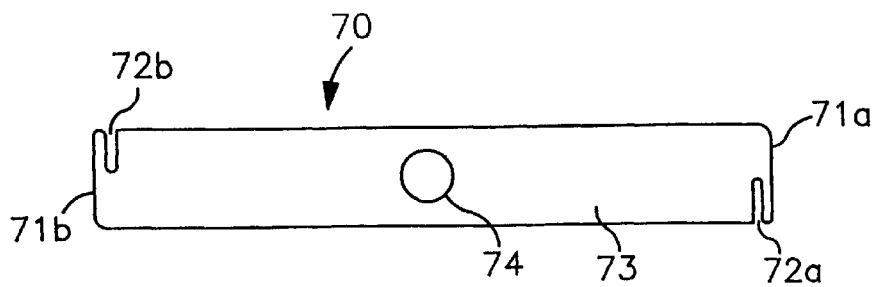
FIG. 8A
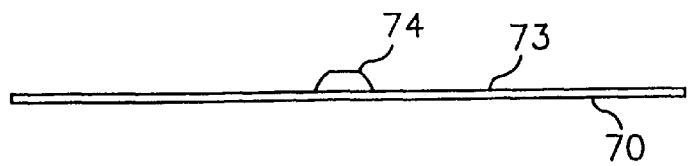
FIG. 8B

APPARATUS AND METHOD FOR EVALUATING CARDIAC FUNCTIONS

CROSS-REFERENCE TO RELATED APPLICATIONS

This application is 371 of PCT/US98/08271 filed Apr. 24, 1998 and a continuation-in-part of prior pending U.S. Ser. No. 09/020,475 filed Feb. 9, 1998, which in turn was a continuation-in-part of U.S. Ser. No. 08/546,246 filed Oct. 20, 1995, now U.S. Pat. No. 5,715,816 issued Feb. 10, 1998, which in turn was a continuation-in-part of U.S. Ser. No. 08/412,287 filed Mar. 28, 1995, now U.S. Pat. No. 5,743,261 issued Apr. 28, 1998, which in turn was a continuation-in-part of U.S. Ser. No. 08/163,052 filed Dec. 6, 1993, now U.S. Pat. No. 5,417,207 issued May 23, 1995; furthermore, this is an application claiming priority on a prior pending Provisional Application, U.S. Serial No. 60/045,006 filed Apr. 25, 1997 and a prior pending Provisional Application, U.S. Serial No. 60/067,810 filed Dec. 5, 1997. The subject matter of each of these is incorporated herein by this reference.

TECHNICAL FIELD

The present invention relates, generally, to the evaluation of cardiac functions, and more particularly to the invasive determination of cardiac output and electrical activity via the use of electrodes placed within the esophagus region of a subject.

BACKGROUND OF THE INVENTION

Electrocardiography, or ECG, involving the collection and study of the electrical activity from the heart, has long been an effective method for the diagnosing and treatment of problems or irregularities related to the operation of the heart. Generally, ECG is used for two major purposes: (1) for diagnosing cardiac arrhythmia's; and (2) providing information on the status of the myocardium.

The early methods for obtaining an electrocardiogram or ECG included the placing of electrodes invasively through the skin or noninvasively attaching the electrodes to the surface of the patient's skin, such as the chest or limbs, by adhesion or clamping. However, certain anatomical disabilities of the human or animal physiology often obstruct the hearts electrical current from the measurement device and thus cause an inaccurate measurement. To avoid these problems, methods were developed for conducting invasive electrocardiograms via the esophagus region.

Esophageal probes for monitoring a patient are, in general known. For example, U.S. Pat. No. RE 31,377, Mylrea et al., reissued Sep. 13, 1983, and U.S. Pat. Nos. 4,349,031 and 4,476,872, Perlin, issued Sep. 14, 1982 and Oct. 16, 1984, respectively, disclose catheters used for monitoring the patients electrocardiogram, heartbeat sounds and temperature. However, disadvantages exist with these probes due to the use of either pill or ring electrodes. Pill electrodes, as shown in FIG. 1A, which are electrodes capable of being swallowed by the patient in an attempt to position the electrodes in the esophagus at the level of the atria, have yielded results that were inconclusive because of variability in electrode placement. Ring electrodes, generally comprised of a conductive band wrapped around the circumference of the probes' flexible tubing, as shown in FIGS. 1B and 1C, can float within the esophagus, and thus, have also yielded inconclusive results for similar reasoning. In particular, when the electrode is not in contact with the tissue wall of the esophagus directly, a fluid or mucosal connection affects the impedance of the received signals, and thus, detrimentally impacts the diagnostic quality of the signals.

Another example, U.S. Pat. No. 3,951,136, Wall, issued Apr. 20, 1976, also discloses an esophageal probe used for monitoring a patient's cardiac electrical activity, heart sounds and temperature wherein the probe disclosed utilizes a pair of spaced electrodes with domed-shaped outer heads. Although these electrodes purport to provide improved contact surface over previously described electrodes, the disclosed electrodes limit and restrict the rotational position of the probe within the esophagus. Moreover, the electrodes configuration suffers from inherent design inadequacies. Further, like the other prior art esophageal probes, the distal end of the probe comprises a thin membrane or diaphragm that seals the end of the probe. As one skilled in the art will appreciate, these thin-walled diaphragms, while effective in allowing for temperature and sound measurements to be obtained, are quite fragile and are often damaged during insertion and use within the patient's esophagus.

Other methods for evaluating cardiac functions are known in the prior art. One particular example, impedance cardiography, is increasingly an important mechanism for determining a patient's cardiac condition both during and following medical procedures.

Impedance cardiography falls within the more general category of impedance plethysmography, which refers to the measurement of volume (and thereby flow) changes in the body, as derived from observing changes in electrical impedance. Impedance cardiography, generally, is a noninvasive bioimpedance method for measuring cardiac output. Specifically, cardiac output measurements are based on the principal that blood is a conductor of electricity and that the electrical impedance of the thorax will change during a cardiac cycle. This change in impedance is caused by the thoracic aortic blood flow which is directly related to the amount of blood ejected from the heart.

U.S. Pat. No. 3,340,867, now Re. 30,101, reissued Sep. 1979 to Kubicek, et al., discloses a method for determining cardiac output by measuring the patient's heart stroke volume. There, an impedance plethysmograph employs two sets of electrodes placed on the neck and chests of patients, to provide an impedance difference signal from the two center electrodes. A constant, low-amplitude, high-frequency alternating current is applied to the outermost pair of electrodes while the innermost pair of electrodes senses the voltage levels above and below the patient's heart. Kubicek et al.'s method entails first determining the heart stroke volume from these impedance signals, based on the observation that resistance to a current passed through the chest varies with thoracic aortic blood flow, and from this determination of stroke volume, then estimating the cardiac output.

U.S. Pat. No. 4,450,527, issued to Sramek on May 22, 1984, generally discloses a similar apparatus, model and equation for relating impedance and stroke volume to determine cardiac output. U.S. Pat. No. 5,309,917, issued May 10, 1994, U.S. Pat. No. 5,423,326 issued Jun. 13, 1995, and U.S. Pat. No. 5,443,073 issued Aug. 22, 1995, all of which were issued to Wang, et al., each generally disclose variations of the Kubicek and Sramek methods.

Yet another model and method of impedance cardiography regarding the placement and spacing of electrodes has been proposed by Bernstein. According to Bernstein, stroke volume (SV) is related to the change in impedance (Z) as shown in Equation 1:

$$SV = \frac{\delta \times \{0.17\ H\}^3 \times T_{LVE} \times (dZ/dt)_{max}}{4.2 \times Z_0} \quad (1)$$

SV=Stroke Volume
δ=correction factor for patient weight
H=Patient height (cm)
$T_{LVE}$=left ventricular ejection time (sec)
$(dZ/dt)_{max}$=maximum value of the first derivative of Z, where Z is the
 change in impedance caused by thoracic aortic blood flow
$Z_0$=mean baseline impedance of the thorax (ohm)

While each these methods can be helpful in determining cardiac output, the various types of non-invasive devices disclosed such as the outer skin electrodes of Kubicek and Sramek, often prove inefficient, for example when dealing with many surgical procedures or with skin abrasion patients. As one can imagine, these devices require a number of exposed connective wires and corresponding electrodes that may interfere with other surgical procedures. Furthermore, because the inner surface electrodes may receive impedance signals from various other regions within the patient due to the distance in placement of the electrodes from the thoracic aorta region, accuracy concerns have been raised. Additionally, incorrect electrode placement can result due to the changes in the patient's physiology of the thorax with respect to the placement of the electrodes on the sternum, as well as due to the size of the patient. Finally, as recognized in Equation 1, a correct factor for patient weight, δ, must be utilized in calculating cardiac output, and often if the weight cannot be accurately determined, the weight estimation can be another source of inaccuracy.

Several of the problems with prior art non-invasive devices have been addressed by more recent developments; however, these new developments still fall short in many critical areas. For example, U.S. Pat. No. 4,836,214, issued to Sramek on Jun. 6, 1989, generally relates to an esophageal probe comprised of an array of electrical bioimpedance ring electrodes provided on a hollow, flexible tube that is insertable into the esophagus of a patient and positioned proximate the descending thoracic aorta. The Sramek device, however, like other non-invasive prior art probes, still permits movement of the probe within the esophagus. As a result of this motion, artifact inaccuracies are possible. This problem is further attenuated by the use of the ring electrodes in that such electrodes often tend to float within the esophagus, as stated previously above.

U.S. Pat. No. 5,357,954, issued to Shigezawa et al. on Oct. 25, 1994, generally relates to an esophageal blood oxygen saturation probe with temperature and sound sensing devices for invasively monitoring a patient. The patent purports to suggest discloses that the internal walls of the esophagus will tend to collapse onto the outer surface of the probe's chassis and sound sensor, such that the probe's sensors will not move appreciably with respect to the esophagus. The ability of the esophagus to prevent undesirable movement of the probe as so disclosed, particularly given the size of the probe, is questioned. Nevertheless, because the probe is not substantially fixed relative to the esophagus, there still exits an opportunity for undesirable movement which, as will be appreciated by those skilled in the art, can lead to inefficient and less accurate results.

Motion limiting devices such as those disclosed in prior oximetry work of the present assignee are known; however, heretofore teachings have not been used in cardiac evaluations, such as impedance cardiography applications. In this regard, the subject matter of application Ser. No. 60/045,006, application Ser. No. , application Ser. No. 08/1546,246 (Pat. No. 5,715,816), application Ser. No. 08/412,287 (Pat. No. ) and Pat. No. 5,417,207 are incorporated herein by reference.

Thus, there exists a long felt need, for an electrode configuration, such as for use in connection with an esophageal probe, which addresses the various deficiencies of the configurations shown in the prior art as discussed herein, including, among other things, inaccurate readings, difficulty in manufacture, reliability in use, fragile construction, and the like. Moreover, there exists a long felt need for an esophageal probe to provide electrodes that remove the variability of electrode placement and contact and provide a concise method of measurement from the esophagus region. Additionally, there exists a need for an esophageal probe that can obtain sound and temperature measurements while evaluating various cardiac functions without the potential for becoming damaged during insertion and use within the patient's esophagus.

SUMMARY OF THE INVENTION

An electrode according to the present invention addresses many of the shortcomings of the prior art. In accordance with the present invention, an electrode useful for generating or receiving electrical signals generally comprises a base and more than one dome-like protuberance arranged on an exterior surface of the base. Further, the electrodes may include connectors configured to enable attachment to a probe for insertion into an anatomical canal of a human or animal.

In accordance with one aspect of the present invention, an electrode assembly may be suitably disposed on an elongated, flexible chassis. The chassis is suitably configured for insertion into the anatomical canal, e.g. esophagus of a patient. Furthermore, the electrode assembly includes the dome-like prominent-arena electrodes for the delivery of alternating current and the sensing of voltage abstract associated with a corresponding impedance variation of the thorax of a patient for determining cardiac output or alternatively for the receiving of electrical signals from the heart (i.e. ECG).

In accordance with a further aspect of the present invention, the probe is suitably configured for insertion in an anatomical canal having a muscle-intensified region, e.g. the crico-pharyngeal region of the esophagus, and as such, includes an engagement device suitably configured for engagement with the muscle-intensified region to substantially secure the probe and the prominent-arena electrodes within the esophagus. Such an engagement device greatly minimizes the probe movement and enhances the accuracy of measurement of electrical signals. The engagement device also serves as a diropter to prevent fluids and other matter from passing-up and being aspirated by the patient.

In accordance with a further aspect of the present invention, the probe is suitably configured to include a temperature measuring device and an acoustic diaphragm for additional monitoring capabilities.

BRIEF DESCRIPTION OF THE DRAWING FIGURES

The present invention will be hereinafter described in conjunction with the appended drawing figures, wherein like designations denote like elements, and:

FIG. 2 is a side view of an electrode in accordance with the present invention;

FIG. 2A is an end view of the electrode of FIG. 2 taken along the lines A—A of FIG. 2;

FIG. 2B is a cross-sectional view of the electrode of FIG. 2 taken along the lines B—B of FIG. 2;

FIG. 3 is a cross-sectional view of a further embodiment of an electrode in accordance with various aspects of the present invention;

FIG. 4 is a cross-sectional view of yet a further embodiment of an electrode in accordance with various aspects of the present invention;

FIG. 5 is a cross-sectional view of a still further embodiment of an electrode in accordance with various aspects of the present invention;

FIG. 6A is a side view of a still further embodiment of an electrode in accordance with the present invention;

FIG. 6B is a side view of yet another embodiment of an electrode in accordance with the present invention;

FIG. 7 is a side view of an electrode in accordance with the present invention which includes an alternative embodiment attachment mechanism;

FIG. 8A shows a top view of an electrode assembly of the present invention illustrating an alternative attachment mechanism.

FIG. 8B is a side view of the electrode assembly of FIG. 8A;

DETAILED DESCRIPTION OF PREFERRED EXEMPLARY EMBODIMENTS

Figure 1B:
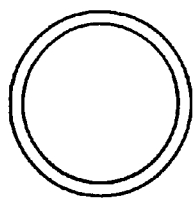
FIG. 1B is an end view of a ring electrode of the prior art.
Figure 1C:
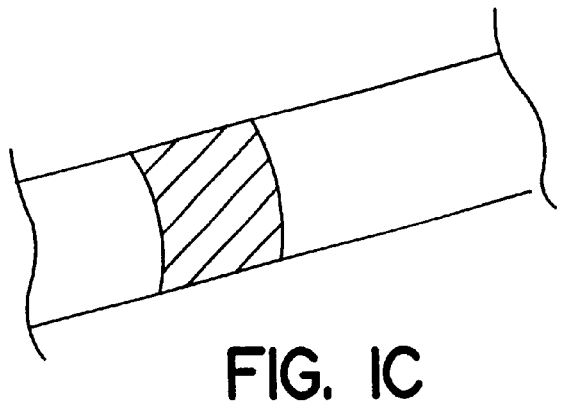
FIG. 1C is a side view of a ring electrode of the prior art.
Figure 1A:
FIG. 1A is a side view of a pill electrode of the prior art.

While the way in which the present invention addresses the disadvantages of the prior art will be described in greater detail hereinbelow, in general, the present invention provides a novel electrode having a configuration which affords many advantages over prior art configurations. As noted hereinabove, conventional ring electrodes are unsatisfactory for most applications in that they exhibit the tendency of being susceptible to errors due to, inter alia, motion artifact and the like. Attempts to address these disadvantages, such as the provision of domed shaped electrodes, for example of the type shown in the Wall '136 patent, are unsuitable because, inter alia, such configurations are susceptible to possible destruction or distortion of the signal due to the multi-component nature of the electrode and/or the inability of properly positioning the electrode within an anatomical canal to generate and/or receive appropriate electronic signals.

Therefore, in accordance with the present invention, and with reference to FIG. 2, the electrodes 17 useful in the context of the present invention preferably include more than one arena electrode dome 50 suitably arranged on a unitary base 52. Preferably, as shown in FIGS. 2, 2A and 2B, base 52 comprises an annular ring having an aperture 54 passing therein. As shown best in FIG. 2B, electrode domes 50 are integrally formed with ring 52, such that when used in connection with a probe configured for insertion into an anatomical canal of a human or animal, anatomical fluids are prevented from penetrating the juncture between dome 50 and ring 52. While in certain applications and aspects of the present invention such a unitary construction may not be necessary, in accordance with a preferred embodiment of the present invention, such construction address various of the shortcomings of prior art configurations.

In accordance with the present invention, dome(s) 50 and ring 52 are suitably comprised of a metal substrate with a desired hardness and corrosion resistance to provide durability. Preferably, dome 50 and ring 52 are comprised of a homogeneous metal that is effective in stabilizing the negative impact in signal quality that can result through the use of metals that are inherently unstable, e.g. an unstable metal can cause the dome 50 and ring 52 to develop different polarities which can lead to inaccurate measurements. In a particularly preferred embodiment of the present invention, dome 50 and ring 52 are comprised of a type 316 stainless steel which has proven durability and corrosion resistance qualities.

With continued reference to FIGS. 2, 2A and 2B, dome 50 preferably has a radius of curvature in the range of 0.050" to 0.090", and more preferably in the range of 0.065" to 0.070" for use in connection with most human and animal esophageal probes. Such a configuration enables the dome to have a sufficiently large surface area. The present inventors have found that domes of such a configuration enhance the reliability of signal data that can be obtained through use of such electrodes. That is, electrodes 17 including domes 50, particularly more than one dome 50, have increased surface area as compared to more conventional ring-type electrodes. As a result, electrodes 17 are better suited for receipt of or sending of signals to or from electrodes 17.

As previously mentioned, electrode 17 preferably includes more than one dome 50. As shown in FIGS. 2A or 2B, a preferred embodiment of electrode 17 includes three electrode domes 50 symmetrically spaced about the circumference of ring 52. As those skilled in the art will appreciate, however, various other configurations are possible. For example, one and one-half domes to more than three domes can be utilized in the context of the present invention. Thus, electrode 17 may also be suitably configured in the form of electrode 17A to include two domes 50 (as shown in FIG. 3), or in the form of electrode 17B to include four domes 50 (as shown in FIG. 4), or five domes (as shown in FIG. 5). As one skilled in the art will appreciate, the number of domes 50 for each electrode 17 is not limited in any manner.

As will be discussed in greater detail herein, the number, configuration and placement of domes 50 about the exterior surface of ring 52 may be selected depending upon any number of factors. For example, as the number of electrodes about the circumference of ring 52 increase, the user is provided with greater accuracy in positioning the electrode within the particular anatomical canal.

Stated another way, and as will be described in connection with a preferred embodiment of the present invention set forth below, when electrodes 17 are used in connection with an ECG or cardiac output probe, the incorporation of multiple domes 50 enable enhanced signal reception and quality.

Preferably, as shown in FIG. 2, electrodes 17 are configured such that when observed from a top perspective view, dome 50 exhibits a generally circular dome shape. It should be appreciated, however, that other shapes, sizes or dimensions may be utilized. In accordance with one aspect of the present invention, dome(s) 50 may exhibit any configuration or shape which either enhances the available surface area of electrode 17 and/or enhances the ability of electrode 17 to contact the wall of the anatomical canal into which it is inserted. Thus, dome 50 may also be configured in various other shapes and/or configurations, including, for example, respective horizontal ellipses 50a or respective vertical ellipses 50b, as shown in FIGS. 6A and 6B. As one skilled in the art will appreciate, the available configurations in the shape of dome 50 are not limited in any manner.

In accordance with the present invention, electrode 17 is suitable for attachment to a probe which is configured for insertion into a human or animal anatomical canal. In accordance with various aspects of the present invention, electrode 17 is suitably configured for attachment to or into such a probe. While various probe embodiments of the present invention will be described in greater detail, hereinbelow, in accordance with one aspect of the present invention, electrode 17 is configured to be attached within a multi-segment probe. For example, with reference to FIG. 2, electrode 17 may suitably comprise a first connector 55a and a second connector 55b located on opposing sides of ring 52. In accordance with this aspect, connectors 55a and 55b are also suitably configured to include an aperture 54 in alignment with aperture 54 of ring 52 (see FIG. 2). Connectors 55a and 55b are suitably configured to enable attachment of electrode 17 to a tube-like probe. While any variety of connection mechanism may be used, in accordance with one embodiment, and as shown in FIG. 2, connectors 55a, 55b are comprised of respective barbs 56a and 56b suitably configured to facilitate connection of electrode 17 to a chassis. Further, in accordance with a particularly preferred aspect, barbs 56a and 56b include multiple components or levels to suitably embed connectors 55a and bbb within a probe.

While in FIG. 2 two such "levels" are shown, it should be appreciated that any number of levels can be utilized. Alternatively, with reference to FIG. 7, instead of connectors 55a and 55b respective threaded sections 57a and 57b may be employed to facilitate connection of electrode 17 to a probe. Further, as one skilled in the art will appreciate, connectors 55a and 55b may also be comprised of various other press-fitting devices and the like to suitably facilitate connection of electrodes 17 to a probe. Still further, various other methods and devices, including, for example, use of adhesives or molding or snap-fitting connectors or any like manner may be utilized in the context of the present invention. As one skilled in the art will appreciate, the attachment devices or methods for connecting electrodes 17 to the probe is not limited in any manner.

Referring now to FIGS. 8A and 8B, and in accordance with another aspect of the present invention, electrode 17 may suitably comprise a band 70 having a first end 71a, a second end 71b, an outside surface 73, and a dome 74. In accordance with this aspect of the present invention, first end 71a and second end 71b each are suitably provided with respective slots 72a and 72b, designed to enable circumferential attachment of band 70 to a probe. In this fashion electrodes may be attached to, as opposed to being imbedded within, a portion of the probe. Band 70 may be either conductive or non-conductive; however, enhanced signal reception is generally available when band 70 is conductive.

Dome 74 is suitably configured to provide electrode 70 with an outer surface to facilitate and maintain direct contact with the esophagus region. In accordance with this preferred aspect, outside surface 73 may be comprised of a plastic-like substrate through which dome 74 comprising a metal material extends. Alternatively, dome 74 may be produced by a mechanical punch formed from outside surface 73 which comprises a metal substrate, or contact surface 74 may be suitably formed and then attached to outside surface 73 of band 70 by any other means, such as, for example, by direct soldering to outside surface 73 of band 70.

Figure 9:
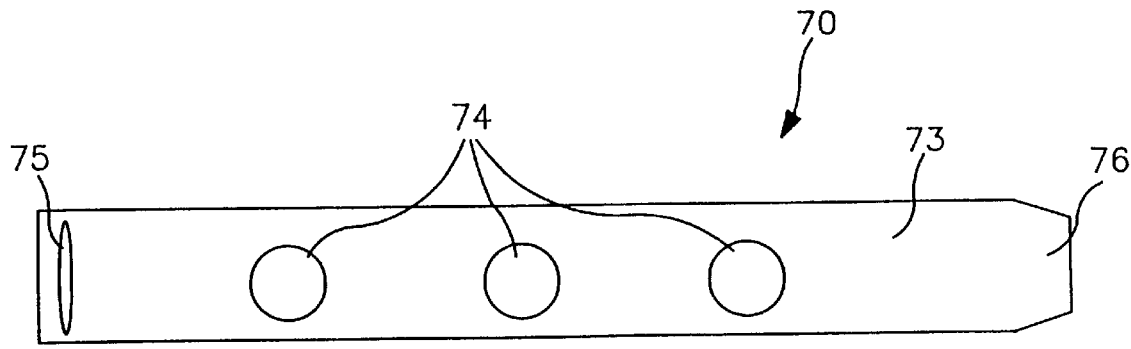
FIG. 9 shows an alternative configuration of the electrode of FIG. 8A in accordance with the present invention.

Various modifications of this connectable band-type electrode will be readily discoverable to those skilled artisans in light of the disclosure thus provided. For example, with reference now to FIG. 9, band 70 may include a plurality of domes 74 such as, for example, three domes as shown. As one skilled in the art will appreciate, the number of domes in this preferred embodiment is not limited in any manner. Additionally, as is also shown in FIG. 9, alternative band attachment configurations may be utilized, such as, for example, by providing band 70 with a slot 75 and angled tab section 76, the insertion of tab 76 into slot 75 which facilitates circumferential attachment of band 70 to a probe. It should be appreciated that bands 70 may be formed in other configurations or attached to a probe in other manners, as is now known or hereafter devised by those skilled in the art.

Figure 10:
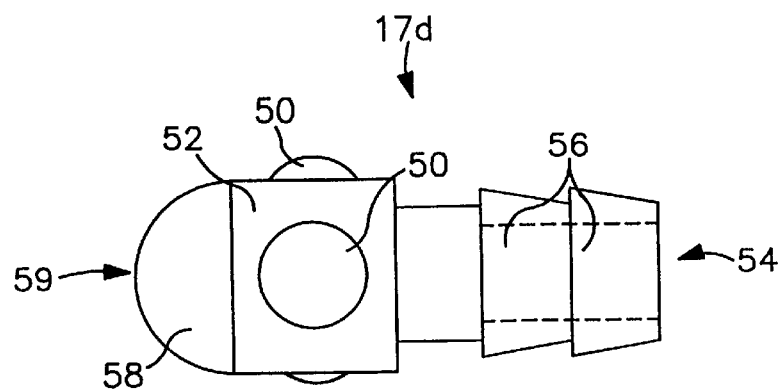
FIG. 10 is a side view of an alternative configuration of the electrode of FIG. 2 in accordance with the present invention.

In accordance with another aspect of the present invention, with reference to FIG. 10, an electrode 17d may be suitably configured to be locatable on the distal end of a probe. Such probes may be more suitable for insertion into the esophagus of a patient. Accordingly, electrode 17d configured for end-attachment preferably includes an end 59 which comprises a generally rounded-portion 58. In this embodiment, due to the durability and hardness of portion 58, the risk of damage to the distal end of the probes, as compared to various prior art probes, may be reduced. Further, electrode 17d may be comprised of a plurality of domes 50, such as is shown in FIG. 9, or alternatively a shown in FIGS. 3, 4 and 5 and previously described herein.

In accordance with the present invention, electrode 17 can be utilized in a variety of applications as will in light of the disclosure herein provided as are now known or may hereafter be devised by those skilled in the art. For example, electrodes of the present invention can be utilized in connection with various ECG, cardiac output or other probe applications.

Figure 11:
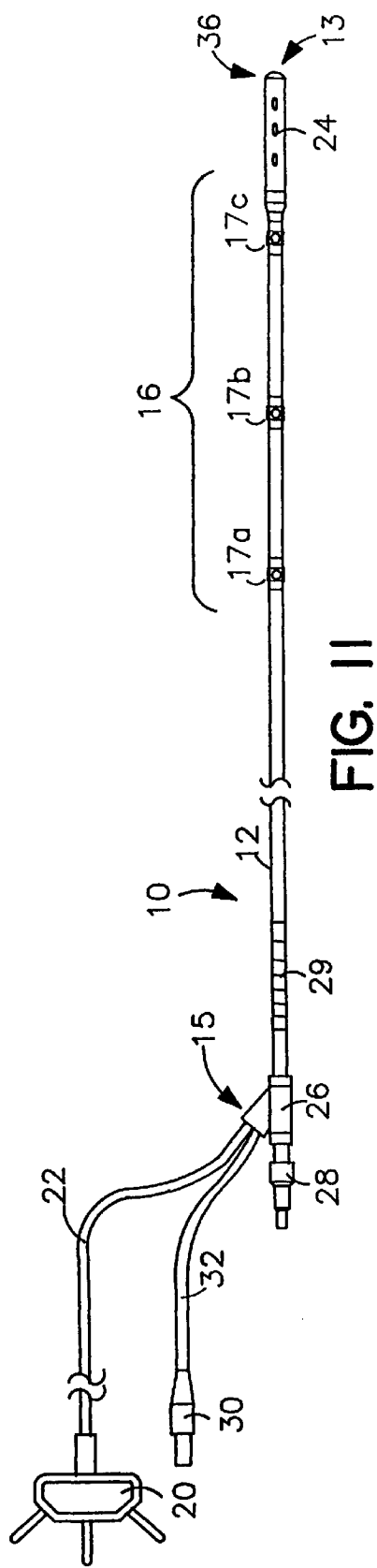
FIG. 11 is a top view of a probe in accordance with one embodiment of the present invention.

Referring now to FIG. 11, in accordance with a preferred embodiment of the present invention, an exemplary probe assembly 10 suitably comprises a chassis 12 having a distal end 13 and a proximal end 15, and an electrode assembly 16. Preferably, electrode assembly 16 is comprised of one or more electrodes 17. In accordance with this preferred embodiment, probe 10 is preferably utilized for electrocardiography or ECG. Accordingly, electrode assembly 16 is suitably interfaced with an electrode plug assembly 20 which is suitably configured for interaction with an electrocardiogram monitor (not shown). Electrode plug assembly 20 may be advantageously attached to chassis 12 via a cable guide 26 which securely grasps an electrode cable 22, and thus, provides a sealed strain relief for connection of electrode cable 22 to corresponding one or more prominent-arena electrodes 17. For purposes of illustration, in this embodiment electrode assembly 16 includes respective electrodes 17a, 17b, and 17c.

As shown, such an exemplary probe assembly 10 may also include other features. In this regard, momentary reference is made to FIGS. 12 and 13, each of which show, as will be described, the orientation of such components. For example, probe 10 preferably may include, in addition to the aforementioned elements, a temperature measuring device 36 and a functional diaphragm 24, and/or various combinations thereof. As shown best in FIGS. 11 and 13, temperature measuring device 36 may be suitably attached to probe 10 proximate distal end 13. Preferably, device 36 comprises a thermistor, preferably of conventional configuration and design, and, as will be appreciated by those skilled in the art, is useful in determining internal body temperature of the patient. With continued reference to FIG. 13, preferably thermistor 36 is suitably attached to a connector 30 for interface with a monitor (not shown) via respective cable sections 32 and 34. As shown best in FIG. 10, preferably section 34 is placed inside of chassis 12, while section 32 preferably, extends exteriorly of chassis 12; preferably, sections 32 and 34 are integrally connected.

Figure 12:
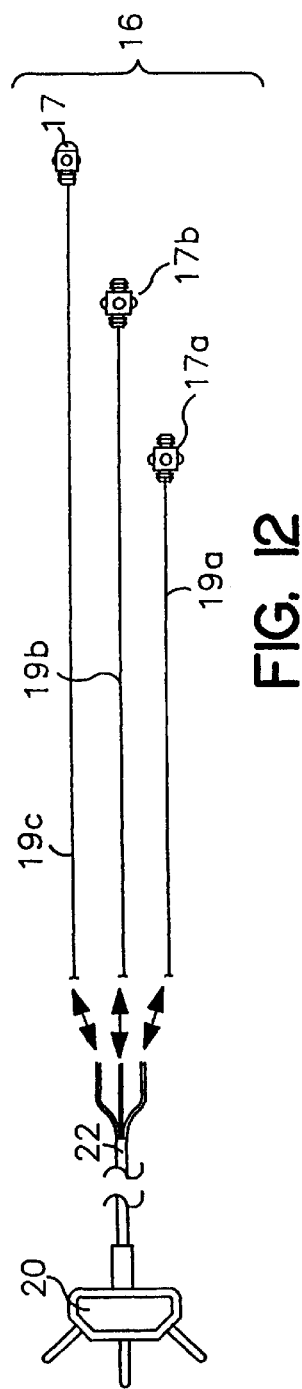
FIG. 12 shows a schematic representation of an electrode assembly in accordance with the present invention.

Referring now to FIG. 12, electrodes 17a and 17b and 17c or 17d are suitably connected to electrode wires, 19a, 19b and 19c, respectively. Preferably, this connection to the electrode wires is by soldering. Furthermore, each electrode wire 19 is fed through chassis 12 and into cable guide 26 for further attachment to electrode cable 22. In accordance with a particularly preferred aspect of this preferred embodiment, each electrode wire may be spiral wound into chassis 12. Furthermore, electrode wires are located within cable 22 which suitably provides a biocompatible sheath for further protection.

With continued reference to FIG. 11, a functional diaphragm 24 may also be provided, and in accordance with this embodiment is located at distal end 13. Functional diaphragm 24 is preferably configured to serve as an acoustic monitor, and thus, is preferably comprised of a thin acoustic material which allows for the efficient transmission of acoustic signals through chassis 12 and into an acoustic adapter 28 located about proximal end 15 of probe. As shown best in FIG. 11, acoustic adapter 28 is suitably mounted on proximal end 15 of probe 10 to interface with a standard medical microphone (not shown). In addition, diaphragm 24 is suitably configured to house thermistor 36 and to seal distal end 13 of probe 10.

Figure 13:
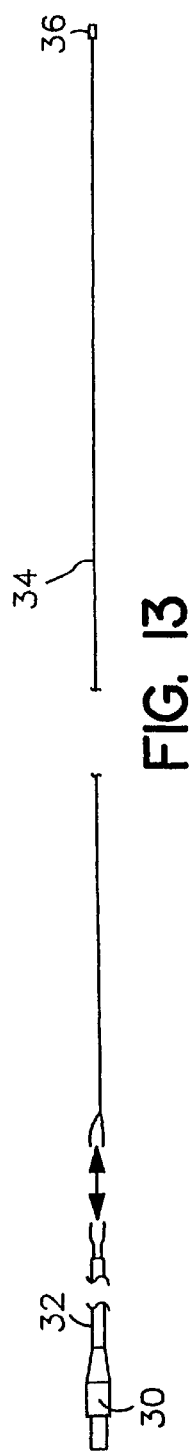
FIG. 13 shows a schematic representation of a temperature measuring device in accordance with the present invention.
Figure 14:
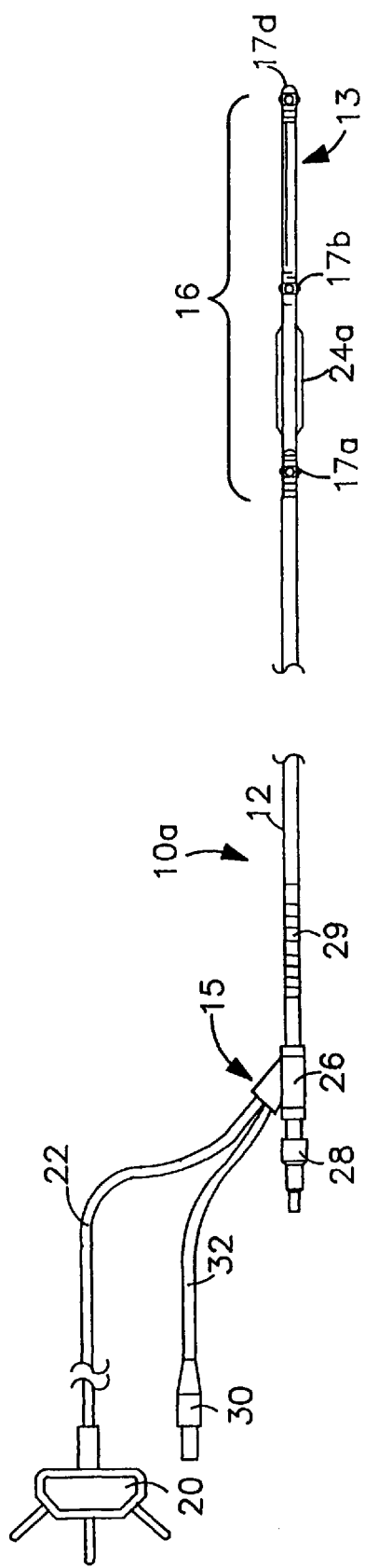
FIG. 14 is an alternative configuration of the probe in accordance with the present invention.

In accordance with another embodiment of the present invention, functional diaphragm 24a may also be suitably positioned at various locations about the length of probe 10. For example, as shown in FIG. 14, a probe 10 may include a diaphragm 24 positioned between an electrode 17a and a distal electrode 17d, and preferably between respective electrodes 17a and 17b. In probe 10A of FIG. 14, elements similar to that of probe 10 shown in FIGS. 11–13 are designated by the same numeric or alphanumeric designation. In accordance with this embodiment, distal electrode 17d facilitates the insertion of probe 10 into the esophagus region with less risk of damage than the probes of the prior art. Further, in accordance with this aspect, thermistor 36 and cable section 34 are suitably configured to be housed within the newly positioned diaphragm 24.

In accordance with the above-described embodiments of the present invention, chassis 12 is suitably configured to be removably inserted into an anatomical canal (e.g. the esophagus) of a human or animal. Chassis 12 is suitably made from any desired biocompatible material, for example, polyurethane, polyethylene, PVC, PTFE, and/or the like. In accordance with a particularly preferred embodiment, chassis 12 is suitably comprised of a flexible resiliency to minimize the danger of lacerating the esophagus during insertion.

Preferably, chassis 12 is of sufficient length to position the various components thereon at optimal positions within the esophageal or other anatomical cavity. In accordance with various aspects of the present invention, chassis 12 evidences a length in the range of about 25 to about 75 cm, and preferably in the range of about 45 to about 65 cm, and most preferably in the range of about 52 to about 54 cm.

In accordance with the present invention, probe 10 is preferably configured such that prominent-arena electrodes 17 are positioned to maintain contact with the wall of the anatomical canal into which probe 10 is utilized. With momentary reference to FIG. 15, for example, when probe 10 is inserted into the esophagus, the preferred configurations of probe 10 enable electrodes 17 to contact with the esophageal wall, generally irrespective of the rotational position of probe 10.

Figure 15:
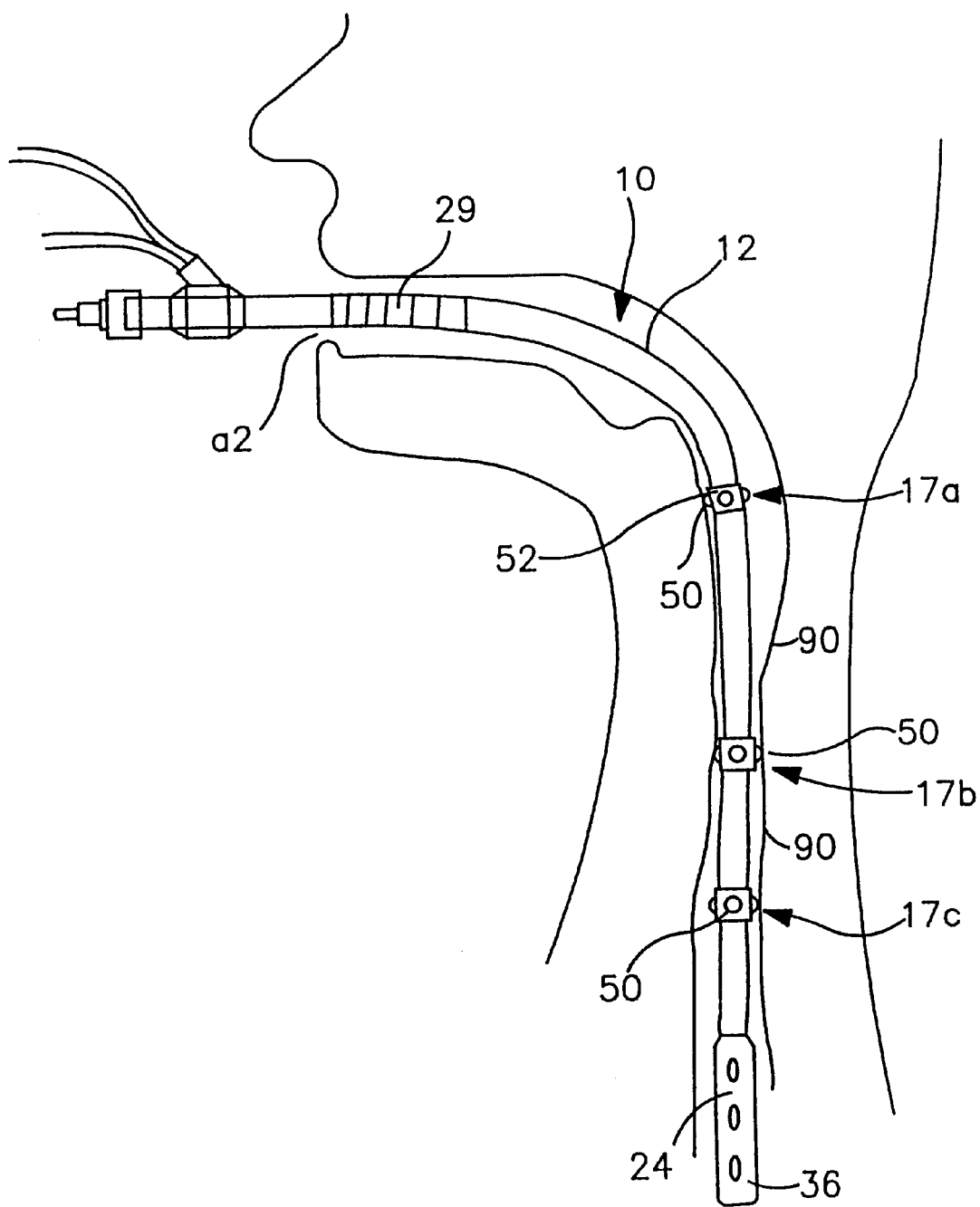
FIG. 15 shows a schematic representation of the probe of FIG. 2 within an anatomical canal (e.g. the esophagus) of a patient.

With reference to FIGS. 11 and 15, to aid in proper insertion of probe 10, chassis 12 may include indicia 29 useful for visually determining when probe 10 has been fully and properly inserted into an anatomical canal. Thus, in accordance with a further aspect of the present invention, probe 10 comprises a depth marker 29 which can serve as an indicator as to when probe 10 is inserted a proper distance. Depth marker 29 suitably may be placed on chassis 12 such that when it is at the mouth area, electrodes 17 are deployed within the esophagus region, and acoustic diaphragm 24 and temperature measuring device 36 are in their appropriate locations. Depth marker 29 may comprise indicia, such as markings, surface impressions, etc., formed on chassis 12. Preferably, depth marker 29 is positioned on chassis 12 a predetermined distance from proximal end 15 in the range of about 7 to about 20 cm, preferably about 10 to about 17 cm, and most preferably about 12 to about 14 cm.

Figure 16:
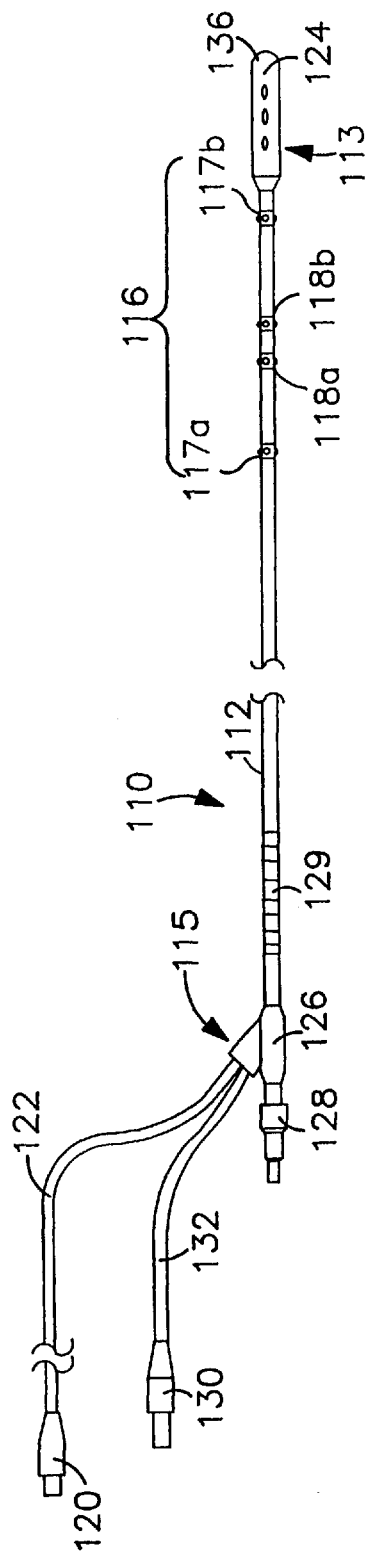
FIG. 16 is a top view of an alternative embodiment of an exemplary probe in accordance with the present invention.

Referring now to FIG. 16, in accordance with another preferred embodiment of the present invention, an exemplary probe assembly 110 useful for measuring the cardiac output of a patient suitably comprises a chassis 112 having a distal end 113 and a proximal end 115, and an electrode assembly 116. Preferably, electrode assembly 116 is comprised of prominent-arena electrodes that include at least a pair of delivery electrodes 117a and 117b, and at least a pair of sensing electrodes 118a and 118b. Electrode assembly 116 is suitably interfaced with an electrode plug assembly 120 which is suitably configured for interaction with a cardiac output monitor (not shown) serving to deliver a constant, low-amplitude, high frequency alternating current to respective delivery electrodes 117a and 117b and receive corresponding voltage signals from respective sensing electrodes 118a and 118b.

In accordance with a preferred exemplary embodiment of the present invention, and similar to probe 10 as previously described above, probe assembly 110 may also include other features. For example, probe 10 preferably may include, in addition to the aforementioned elements, a temperature measuring device 136 and a functional diaphragm 124, and/or various combinations thereof.

With continued reference to FIG. 16, functional diaphragm 124 may be located at distal end 113. Alternatively, functional diaphragm (not shown) may be suitably positioned between one or more of electrodes 117 and 118.

Electrodes 117a and 117b and electrodes 118a and 118b are suitably configured to be integral with chassis 112 such that probe 110 can deliver alternating current and then detect a voltage abstract associated with an impedance variation of the thorax, with the results measured at a cardiac output monitor (not shown). Preferably, delivery electrode 117a is positioned near a mid-region of probe 110 while delivery electrode 117b is positioned in proximity to distal end 113 of probe 110. Furthermore, sensing electrodes 118a and 118b are positioned in between delivery electrodes 117a and 117b, and are spaced approximately equivalent to a patient's heart, to suitably receive the appropriate voltage abstract associated with the impedance variation of the thorax.

In accordance with the present embodiment of the present invention, electrodes 117a, 117b, 118a, and 118b are suitably comprised of the various embodiments for electrodes as set forth in FIGS. 2 through 8 above and previously described herein. Furthermore, in accordance with the present embodiment, other electrodes, as are now known or hereafter devised by those skilled in the art, may be suitably utilized in probe 10 in accordance with the present invention.

In accordance with the present invention, and as fully disclosed in commonly assigned pending application U.S. Ser. No. 08/546,246, entitled, "Improved-Oximeter Probes and Methods for the Invasive Use Thereof", the probe assemblies of the present invention may be suitably configured to ensure that such probes are effectively stabilized within a body cavity. For example, by enlarging the diameter of the chassis 12 or otherwise deploying prominent-arena electrodes 17 and/or 18 of probe 10 into engagement with a wall of the anatomical canal into which the probe is inserted, a certain degree of stabilization may be obtained.

However, in accordance with another aspect of the present invention, the probes disclosed herein may be configured such that the prominent-arena electrodes are positioned and maintained in a region proximate the thoracic aorta. For example, the present inventors have found that locking the probe in a muscular region of a body canal enables the measurement of bioimpedence signals which is relatively unaffected by movements. In accordance with a preferred aspect, the muscle targeted comprises a sphincter-type muscle, such as, the crico-pharyngeal (CP) muscle in the esophagus. As will be appreciated, such sphincter-type muscles function, such as when food or other objects approach the muscle, to contract and dilate thereby allowing the objects to pass. After the objects pass, the muscle again relaxes and constricts.

Thus, in accordance with the various aspects of this embodiment of the invention, the probes disclosed herein may be suitably configured to take advantage of the dilation and constriction of such muscle, e.g. the CP or other similar muscle, to secure and stabilize the probe within the anatomical canal, thus tending to inhibit movement of the probe while obtaining reliable bioimpedence readings. Such a configuration also serves to act as an esophageal diopter, preventing fluids and other matter from passing up and being aspirated by a patient. The use of engagement devices of this type in connection with esophageal oximetric applications is disclosed in U.S. Pat. No. 5,715,816 issued Feb. 10, 1998, the subject matter of which, as previously noted, is incorporated by reference herein. While the '816 does not describe use of such a device in connection with ECG or cardiac monitors of the type disclosed herein, the present inventors have found that such a device may have usefulness. In view of the incorporation of the subject matter of that reference into this document, the particulars of the engagement device will not herein be described. However, for purposes of illustration, an exemplary probe with use of such an engagement device will now be described. Specifically, referring now to FIG. 17, and in accordance with a preferred aspect of this embodiment of the present invention, a probe 210 may be provided with an engagement device 214 of the type described in the '816 patent.

Figure 17:
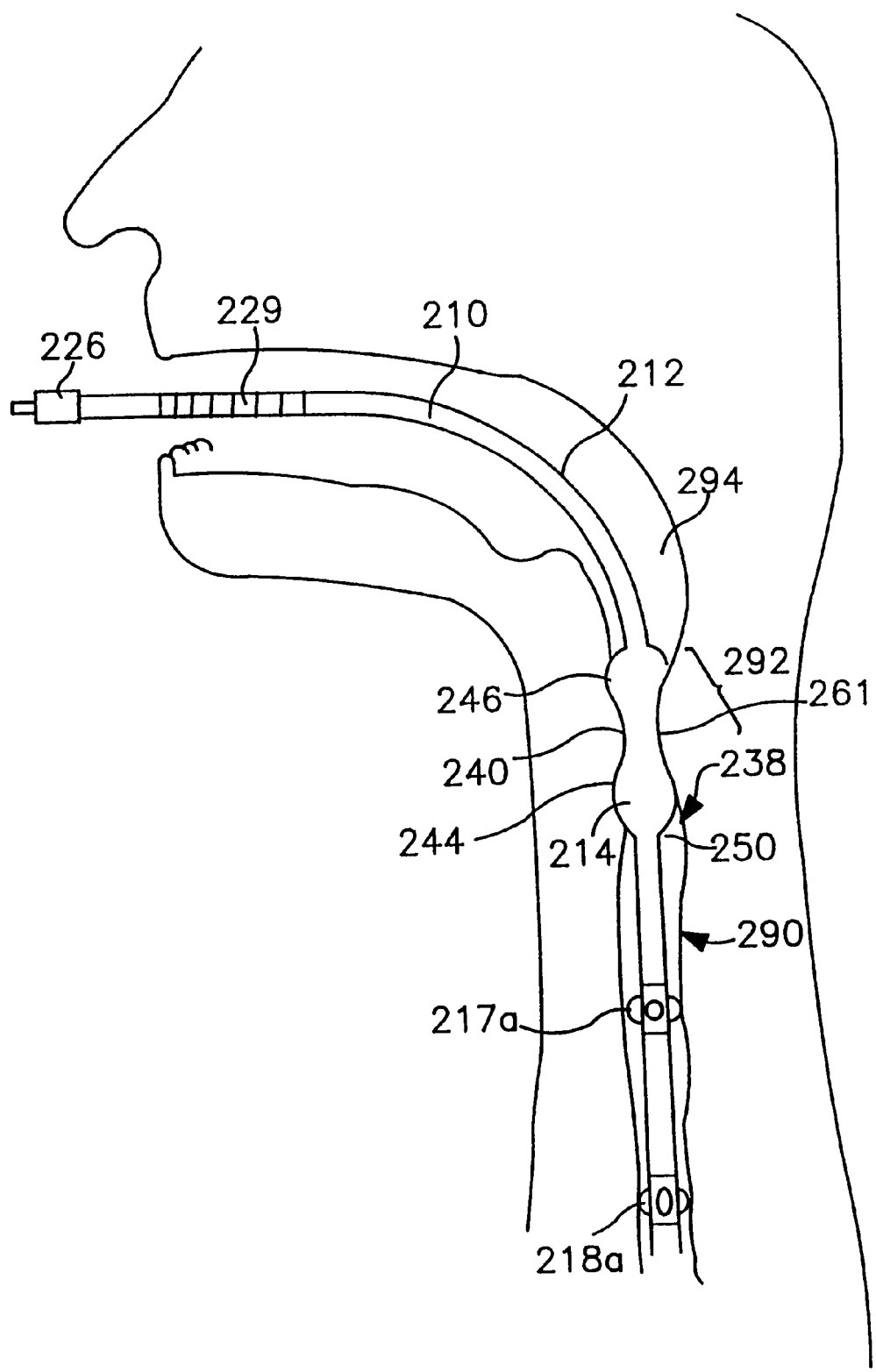
FIG. 17 shows a schematic representation of the probe of FIG. 15 within an anatomical canal (e.g. the esophagus) of a patient.

To aid in the description of this aspect of the present invention, and with continued reference to FIG. 17, the use of device 214 will now be briefly described. When a probe 210 including engagement device 214 is inserted into an anatomical canal, e.g. the esophagus, leading edge 250 enters into a muscle region, e.g. the CP muscle region, thereby causing the CP muscle to contract and dilate. This dilation advantageously allows first segment 238 of engagement device 14 to enter the CP muscle region. Continued insertion of the probe, and thus device 14 into the canal, e.g. the esophagus, causes lobe 244 to contract and interact with the CP muscle; through appropriate dimensioning of lobe 244, such interaction causes the CP muscle to relax and constrict. This constriction together with further insertion of the probe tends to cause the CP muscle to constrict further and substantially surround joining section 240 about region 261. Further insertion of probe 10 thus tends to be inhibited, in large part due to the appropriate dimensioning of lobe 246. With further movement inhibited, said pairs of delivery and sensing electrodes are suitably deployed into the esophagus. Lobes 244 and 246 thus prevent engagement device 214 from migrating up or down the esophagus once probe 210 is in place thereby allowing substantially stable bioimpedence measurements.

The various dimensions and configurations of the various surfaces of device 214 may be optimized from that which is disclosed in the '816 patent to aid in utilization of probe 210 including device 214.

Specifically, it should be appreciated that device 214 suitably may evidence a wide variety of different configurations, providing such configurations also enable proper placement and securing of probe 210 in a suitable region of the anatomical canal in which probe 210 is inserted. Thus, alterations and modifications of the dimensions and configurations of the various segments and regions of device 214 may be made, as will be appreciated or as may be hereafter devised by those skilled in the art in light of this disclosure.

With reference again to FIG. 17, in accordance with a preferred aspect of this embodiment of the present invention, device 214 is suitably employed in connection with probe 210 such that effective and reliable bioimpedence measurements are obtained when probe 210 is inserted into the esophagus; that is, insertion of probe 210 into the patient results in effective placement of electrode assemblies 17, 18 proximate the esophagus.

To aid in proper insertion of probe 210, chassis 212 may include indicia useful for visually determining when probe 210 has been fully and properly inserted into an anatomical canal including a depth marker 229, as previously described herein, which can serve as an indicator as to when probe 10 is inserted a proper distance.

A preferred manner of inserting probe 210 into a patient will now be described with continued reference to FIG. 17.

In accordance with a preferred embodiment of the present invention, a person (e.g. doctor, technician, etc.) will insert probe 210 through the mouth and into an esophageal cavity 290 of a patient causing the leading edge (not shown) to pass down esophagus 290 to and through the CP muscle region 292. As probe 210 is further inserted, engagement device 214 is directed toward CP muscle 292. Because engagement device 214 is larger than chassis 212, leading edge of engagement device 214 will generally stretch the membrane that precedes (i.e. is above) muscle 292, thereby causing activation of the neurons in the muscle and thus relaxation (i.e. dilation) of muscle 292. Continued insertion of probe 210 results in lobe 244 being passed through muscle 292, which in turn tends to cause muscle 292 to contract and generally surround segment 240 of device 214. While insertion of probe 210 may halt at that point, preferably probe 210 is further inserted such that lobe 246 is also passed through muscle 292. In accordance with this aspect of the present invention, to thus set engagement device 214 of probe 210 in place, the direction of probe 210 is thereafter reversed such that lobe 246 backs up through CP muscle 292. Such movement tends to cause CP muscle 292 to relax and constrict upon segment 240. This constriction of muscle 292 tends to "lock" device 214 in place thus tending to deploy said delivery and sensing electrodes in an ideal location. In addition, due to the orientation of the elements of probe 120, once device 214 is suitably positioned, acoustic diaphragm 24 and thermistor 36 will also be suitably positioned further within esophagus 90. This approximate positioning may be evident by alignment of a depth marker 29 within the mouth of the patient.

It will be understood that the foregoing description is of preferred exemplary embodiments of the invention, and that the invention is not limited to the specific forms shown. Various modifications may be made in the design and arrangement of the elements set forth herein without departing from the scope of the invention as expressed in the appended claims.

We claim:

1. An electrode useful for generating or receiving electrical signals, the electrode comprising:
   a base; and
   more than one protuberance unitarily arranged on said base, wherein said protuberances are dome-like, and wherein each said protuberance is configured for facilitating contact with a tissue wall of the esophagus of a patient.

2. An electrode in accordance with claim 1, wherein said protuberances comprise one and one-half domes.

3. An electrode configured for facilitating contact with a tissue wall of the esophagus of a patient, the electrode comprising:
   an annular ring base having an exterior surface and an interior aperture; and
   a plurality of domes arranged on said exterior of said base.

4. An electrode in accordance with claim 3, wherein said domes comprise three domes arranged symmetrically about said base exterior.

5. An electrode in accordance with claim 4, wherein said domes have a radius of curvature in the range of 0.050" to 0.090".

6. An electrode in accordance with claim 4, wherein said domes and said ring comprise a homogeneous metal.

7. An electrode in accordance with claim 3, wherein said domes have a radius of curvature in the range of 0.050" to 0.090".

8. An electrode in accordance with claim 7, wherein said domes have a radius of curvature in the range of 0.065" to 0.070".

9. An electrode in accordance with claim 3, wherein said domes are integrally formed with said ring base, such that when used in connection with a probe configured for insertion into an anatomical canal comprising the esophagus of a human or animal, anatomical fluids are prevented from penetrating between a juncture defined by said domes and said ring base.

10. An electrode in accordance with claim 3, wherein said electrode further comprises a first connector and a second connector located on opposing sides of said ring, said first and said second connectors configured to enable attachment of said electrode to a tube-like probe.

11. An electrode in accordance with claim 10, wherein each of said first and said second connectors comprise at least one barb to facilitate attachment to said tube-like probe.

12. An electrode in accordance with claim 11, wherein each of said first and said second connectors comprise a threaded section to facilitate attachment to said tube-like probe.

13. An electrode in accordance with claim 3, wherein said electrode further comprises an end having a rounded-portion configured for insertion into an anatomical canal comprising the esophagus of a human or animal.

14. An electrode in accordance with claim 13, wherein said electrode further comprises a connector located on a side opposing said rounded portion and configured to enable attachment of said electrode to a distal end of a tube-like probe.

15. An electrode configured for use within the esophagus of a patient, the electrode comprising:
   a band having an outside surface; and
   at least one dome unitarily mounted on said outside surface, wherein said at least one dome is configured for facilitating contact with a tissue wall of the esophagus of a patient.

16. An electrode in accordance with claim 15, wherein said electrode further comprises a means for facilitating circumferential attachment of said band to a probe.

17. An electrode in accordance with claim 15, wherein said electrode comprises a plurality of domes.

* * * * *